(12) United States Patent
Deavenport et al.

(10) Patent No.: US 7,541,496 B2
(45) Date of Patent: Jun. 2, 2009

(54) PROCESS FOR PREPARING DIHYDROXYTRIALKYLAMMONIUM HALIDES AND PRODUCTS THEREOF

(75) Inventors: Joseph L. Deavenport, Lake Jackson, TX (US); Rhonda C. Posey, Brazoria, TX (US); David A. Wilson, Lake Jackson, TX (US)

(73) Assignee: Dow Global Technologies Inc., Midland, MI (US)

( * ) Notice: Subject to any disclaimer, the term of this patent is extended or adjusted under 35 U.S.C. 154(b) by 0 days.

(21) Appl. No.: 11/403,779

(22) Filed: Apr. 13, 2006

(65) Prior Publication Data

US 2007/0299284 A1    Dec. 27, 2007

Related U.S. Application Data

(60) Provisional application No. 60/773,536, filed on Feb. 15, 2006.

(51) Int. Cl.
*C07C 223/00* (2006.01)
*C07C 215/00* (2006.01)
*C07C 209/00* (2006.01)

(52) U.S. Cl. .................. 564/296; 564/281; 564/292
(58) Field of Classification Search .......... 564/281, 564/292, 296
See application file for complete search history.

(56) References Cited

U.S. PATENT DOCUMENTS

| | | | |
|---|---|---|---|
| 4,137,180 A | | 1/1979 | Naik et al. |
| 4,675,131 A | | 6/1987 | Walraevens et al. |
| 5,372,643 A | | 12/1994 | Gosset et al. |
| 5,463,127 A | * | 10/1995 | Deavenport et al. ......... 564/292 |
| 6,120,554 A | | 9/2000 | Patton et al. |

FOREIGN PATENT DOCUMENTS

| | | | |
|---|---|---|---|
| DE | 195 17 048 C1 | | 5/1995 |
| EP | 0 257 619 B1 | | 7/1991 |
| GB | 1335760 | * | 10/1973 |
| JP | 01 233264 A | | 9/1989 |
| WO | WO 2006/045471 A | | 5/2006 |

OTHER PUBLICATIONS

Wang et al., Synthesis of Polyesers Having Quaternary Ammonium Groups in Side chans and Preparation of Their Glends with Poly (vinyl Alcohol), 1994, Journal of Polymer Science Part A: Polymer Chemistry Edition 32, No. 7, pp. 1256.*

A. W. Moyer and Vincent Du Vigneaud: "The Structural Specificity of Choline and Betaine in Transmethylation" The Journal of Biological Chemistry, 1942, pp. 373-382.

C. Wang, et al.; "Synthesis of Polyesters Having Quaternary Ammonium Groups in the Side Chains and Preparation of Their Blends with Poly (vinyl Alcohol)", Journal of Polymer Science, Part A: Polymer Chemistry Edition, Interscience Publishers, New York, NY, US, vol. 32, No. 7, May 1, 1994, pp. 1255-1262.

R. J. Goddard and S. L. Cooper: "Polyurethane Cationomers with Pendant Trialkylammonium Groups: Effects of Ion Content, Alkyl Group, and Neutralizing Anion", Journal of Polymer Science, Part B: Polymer Physics, vol. 32, 1994, pp. 1557-1571.

J. D. Triggle, et al., "Studies on the Chemical Basis for Cholinomimetic and Cholinolytic Activity, Part I, the Synthesis and Configuration of Quaternary Salts in the 1,3-Dioxolane and Oxazoline Series", Canadian Journal of Chemistry, National Research Council, Ottawa, CA, vol. 40, 1962, pp. 1201-1215.

Mikael, Bols, et al., "Simple Synthesis of (R)-Carnitine from D-Galactono-1, 4-lactone", Tetrahedron, vol. 48, No. 2, 1992, pp. 319-324.

* cited by examiner

*Primary Examiner*—Porfirio Nazario-Gonzalez
*Assistant Examiner*—Yate' K Cutliff

(57) ABSTRACT

Compositions and methods for making compositions including a quaternary trialkylammonium halide compound are described. Compositions follow the formula:

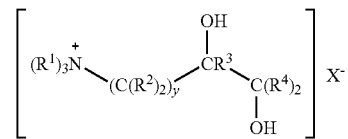

wherein the $R^1$ groups are each individually selected from alkyl groups having from 1 to 12 carbon atoms; wherein the $R^2$, $R^3$, and $R^4$ groups are each individually selected from hydrogen, hydroxide, alkyl groups having from 1 to 12 carbon atoms, and hydroxy alkyl groups having from 1 to 12 carbon atoms; wherein y ranges from 0 to 12; wherein $X^-$ is selected from fluoride, chloride, bromide, and iodide; wherein the quaternary trialkylammonium compound is present in an amount of at least 90 wt. percent; and wherein the composition comprises not greater than 4000 ppm of a trialkylamine or protonated form thereof.

22 Claims, No Drawings

PROCESS FOR PREPARING DIHYDROXYTRIALKYLAMMONIUM HALIDES AND PRODUCTS THEREOF

PRIOR RELATED APPLICATIONS

This application claims priority to U.S. Prov. Appl. Ser. No. 60/773,536 filed on Feb. 15, 2006 entitled "Process for Preparing Dihydroxytrialkylammonium Halides and Products Thereof" which is incorporated herein by reference in its entirety.

FEDERALLY SPONSORED RESEARCH STATEMENT

Not applicable.

REFERENCE TO MICROFICHE APPENDIX

Not applicable.

FIELD OF THE INVENTION

The invention relates to quaternary trialkylammonium halide compositions and methods for making such compositions. Specifically, embodiments of the invention provide compositions comprising a quaternary trialkylammonium halide compound following the formula:

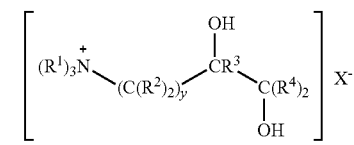

BACKGROUND OF THE INVENTION

Quaternary trialkylammonium compounds have a variety of commercial applications in the textile industry and in the personal care arena. Some of these compounds can also be used as anti-microbial agents; in modifying fillers, fibers, and surfaces; as thickening agents; and as conditioning agents.

In many of these applications and uses, it is desirable to provide the quaternary trialkylammonium compound in a high purity form to ensure that undesirable effects of impurities are minimized. Conventional compositions either lack acceptable concentrations of the quaternary trialkylammonium compounds while possessing more or less innocuous impurities while other products may have higher concentrations of the quaternary trialkylammonium halide compounds but also possess undesirable amounts of more noticeable impurities. One such impurity is residual trialkylamine because they have a characteristically unpleasant odor. For example, the human nose can detect a fishy odor when, one such amine, trimethylamine is present in concentrations as low as about 0.0023 ppm. Thus, quaternary trialkylammonium halides prepared from such trialkylamine precursors often possess offensive odors even when diluted in formulations. Consequently, compositions having higher concentrations of the quaternary trialkylammonium halide and reduced levels of impurities, as well as processes for preparing such compounds by more efficient methods, would be useful.

SUMMARY

In some embodiments, the invention provides compositions that comprise a quaternary trialkylammonium halide compound following the formula:

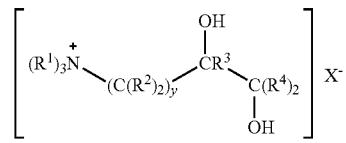

wherein the $R^1$ groups are each individually selected from the group consisting of alkyl groups having from 1 to 12 carbon atoms; wherein the $R^2$, $R^3$, and $R^4$ groups are each individually selected from the group consisting of hydrogen, hydroxide, alkyl groups having from 1 to 12 carbon atoms, and hydroxy alkyl groups having from 1 to 12 carbon atoms; wherein y ranges from 0 to 12; wherein $X^-$ is selected from the group consisting of fluoride, chloride, bromide, and iodide; wherein the quaternary trialkylammonium compound is present in an amount of at least 90 wt. percent; and wherein the composition comprises not greater than 4000 ppm of a trialkylamine or protonated form thereof.

Particular compositions have at least 99.5 wt. percent 2,3-dihydroxypropyltrimethylammonium chloride and not greater than 25 ppm trimethylamine, wherein the concentrations are determined based on the amounts of 2,3-dihydroxypropyltrimethylammonium chloride and the trimethylamine in the composition.

Other embodiments provide a method of making a quaternary trialkylammonium halide composition. In some embodiments, the method includes providing a primary-halo-dihydroxyalkane and a trialkylamine in a stoichiometric excess with respect to the primary-halo-dihydroxyalkane under reaction conditions to provide an intermediate reaction mixture; reducing the pH of the intermediate reaction mixture; and isolating the quaternary trialkylammonium halide composition.

In some embodiments, the method includes a method of making a 2,3-dihydroxypropyltrimethylammonium chloride composition. Methods of making 2,3-dihydroxypropyltrimethylammonium chloride compositions include providing 3-chloro-1,2-dihydroxypropane and trimethylamine in a molar ratio of 1 to about 3 moles with respect to the 3-chloro-1,2-dihydroxypropane under reaction conditions to provide an intermediate reaction mixture; removing at least a portion of the remaining trimethylamine from the intermediate reaction mixture; and isolating the 2,3-dihydroxypropyltrimethylammonium chloride composition.

In certain embodiments of the methods described herein, the method does not include heating the intermediate reaction mixture to remove one or more volatile components. In some embodiments, the method does not include heating the intermediate reaction mixture to remove volatile components when the reaction mixture has a pH of 8 or more.

DESCRIPTION OF EMBODIMENTS OF THE INVENTION

In the following description, all numbers disclosed herein are approximate values, regardless whether the word "about"

or "approximate" is used in connection therewith. They may vary by 1%, 2%, 5%, and sometimes, 10 to 20%. Whenever a numerical range with a lower limit, RL and an upper limit, RU, is disclosed, any number falling within the range is specifically disclosed. In particular, the following numbers within the range are specifically disclosed: R=RL+k*(RU−RL), wherein k is a variable ranging from 1% to 100% with a 1% increment, i.e., k is 1%, 2%, 3%, 4%, 5%, . . . 50%, 51%, 52%, . . . 95%, 96%, 97%, 98%, 99%, or 100%. Moreover, any numerical range defined by two R numbers as defined in the above is also specifically disclosed.

The process of the invention is widely applicable and is particularly useful for preparation of 3-chloro-1,2-dihydroxypropyltrimethylammonium chloride from trimethylamine reacted with 3-chloro-1,2-dihydroxypropane. While the description is partially given in terms of that specific example for clarity, the invention is not so limited.

Thus, embodiments of the invention provide a composition comprising a quaternary trialkylammonium halide compound following the formula:

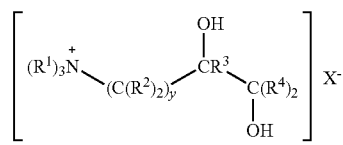

wherein the $R^1$ groups are each individually selected from the group consisting of alkyl groups having from 1 to 12 carbon atoms; wherein the $R^2$, $R^3$, and $R^4$ groups are each individually selected from the group consisting of hydrogen, hydroxide, alkyl groups having from 1 to 12 carbon atoms, and hydroxy alkyl groups having from 1 to 12 carbon atoms; wherein y ranges from 0 to 12, preferably y ranges from 0 to 6, more preferably y ranges from 0 to 3, most preferably y is 1; wherein $X^-$ is selected from the group consisting of fluoride, chloride, bromide, and iodide, preferably $X^-$ is chloride; wherein the quaternary trialkylammonium compound is present in an amount of at least 90 wt. percent; and wherein the composition comprises not greater than 4000 ppm of a trialkylamine.

In particular embodiments, the quaternary trialkylammonium compound comprises at least 90 wt. percent to 100 percent of the composition. Compositions of other embodiments have higher concentrations of the quaternary trialkylammonium compounds, such as 92.5 wt. percent, 95 wt. percent, 97.5 wt. percent, 99 wt. percent, 99.5 wt. percent, 99.95 wt. percent, 99.99 wt. percent, or 99.995 wt. percent of the quaternary trialkylammonium compound in the composition.

While concentration of the trialkylamine in the compositions is typically not greater than about 4000 ppm, other compositions have a lower concentration of the trialkylamine. In some embodiments, the concentration of trialkylamine is less than about 4000 ppm, less than about 3000 ppm, less than about 2500 ppm, less than about 2000 ppm, less than about 1000 ppm, less than about 500 ppm, less than about 400 ppm, less than about 300 ppm, less than about 200 ppm, less than about 100 ppm, less than about 50 ppm, less than about 25 ppm, less than about 10 ppm, less than about 5 ppm, less than about 1 ppm, less than about 0.1 ppm, less than about 0.01 ppm, less than about 0.002, or less than about 0.001 ppm. In particular embodiments, the concentration of the trialkylamine or protonated form of the amine is present in an amount ranging from about 1 ppm to about 100 ppm. In other embodiments, the concentration of the trialkylamine or protonated form of the amine is present in an amount ranging from about 10 ppm to about 25 ppm, preferably about 1 ppm to about 10 ppm.

In some compositions, the quaternary trialkylammonium compound is present in an amount of at least 95 wt. percent; and wherein the composition comprises not greater than 1000 ppm of the trialkylamine or protonated form thereof. In other embodiments, the quaternary trialkylammonium compound is present in an amount of at least 99.5 wt. percent and the composition comprises not greater than 500 ppm of the trialkylamine or the protonated form thereof. In still other embodiments, the quaternary trialkylammonium compound is present in an amount of at least 99.5 wt. percent and the composition comprises not greater than 500 ppm of the trialkylamine or the protonated form of the trialkylamine. In yet other embodiments, the quaternary trialkylammonium compound is present in an amount of at least 99.5 wt. percent and the composition comprises not greater than 100 ppm, not greater than 25 ppm, or not greater than 10 ppm, of the trialkylamine or the protonated form thereof. In particular embodiments, the composition comprises at least 99.9 wt. percent of the quaternary trialkylammonium compound and not greater than 1 ppm of the trialkylamine or the protonated form thereof.

It is envisioned that the compositions of embodiments of the invention may be combined with other components to provide a suitable composition for personal care uses. Thus, the amounts or concentrations of the quaternary trialkylammonium compound and the trialkylamine compound in the composition may be determined as an absolute value in the composition or relative to only the amounts of the quaternary trialkylammonium compound and the trialkylamine compound in the composition.

The term "alkyl group" as used herein is intended to include hydrocarbon-containing groups having 1 to 12 carbon atoms including alkyl groups, substituted or branched alkyl groups, or substituted or branched aryl groups, particularly groups having from 1 to about 6 carbon atoms, such as methyl and ethyl groups. Thus, in some embodiments, each $R^1$ groups is individually selected from alkyl groups having from 1 to 12 carbon atoms, preferably 1 to about 6, more preferably 1 to 3 carbon atoms, most preferably 1 carbon atom. Likewise, where the $R^2$, $R^3$, and $R^4$ groups are alkyl groups, they are are each individually selected from the group consisting of alkyl groups having from 1 to 12 carbon atoms, 1 to about 6, 1 to 3 carbon atoms, or 1 carbon atom. Thus such alkyl groups may include substituted alkyl, or aryl group, particularly groups having from about 1 to about 6 carbon atoms. In some embodiments, $R^2$, $R^3$, and $R^4$ may be hydrogen, hydroxide, or hydroxy alkyl groups having from 1 to 12 carbon atoms. In particular other embodiments one or more of the $R^2$, $R^3$, or $R^4$ groups may be a hydroxyalkyl group having from 1 to 4 carbon atoms, preferably hydroxymethyl or hydroxyethyl groups; hydrogen, or a hydroxyl group.

While some embodiments include any combination of alkyl groups as the $R^1$ groups, in particular embodiments each $R^1$ group is the same alkyl group, for example, providing a composition that includes a trimethylammonium-, triethylammonium-, or tri-n-propylammonium compound. In particular compositions the quaternary trialkylammonium compound is a 2,3-dihydroxypropyltrialkylammonium chloride or 3,4-dihydroxybutyltrialkylammonium chloride. Some compositions comprising 2,3-dihydroxypropyltrimethylammonium chloride are preferred.

Particular compositions provide 2,3-dihydroxypropyltrimethylammonium chloride wherein the 2,3-dihydroxypropyltrimethylammonium chloride is present in an amount of at least 95 wt. percent; and wherein the composition comprises not greater than 1000 ppm of the trimethylamine or protonated form thereof. In other compositions, the 2,3-dihydroxypropyltrimethylammonium chloride is present in an amount of at least 99.5 wt. percent; and the composition comprises not greater than 500 ppm of the trimethylamine or the protonated form thereof. In still other compositions, the 2,3-dihydroxypropyltrimethylammonium chloride is present in an amount of at least 99.5 wt. percent and wherein the composition comprises not greater than about 250 ppm, not greater than about 100 ppm, not greater than about 50 ppm, not greater than about 25 ppm, not greater than about 10 ppm, not greater than about 5 ppm, not greater than about 1 ppm, not greater than about 0.1 ppm, not greater than about 0.002 ppm, not greater than about 0.001 ppm of the trimethylamine or the protonated form thereof, particularly trimethylamine. Some compositions comprise at least 99.9 wt. percent, 99.95, 99.99, or 99.995 wt percent 2,3-dihydroxypropyltrimethylammonium chloride and not greater than 1 ppm of the trimethylamine or the protonated form thereof, particularly trimethylamine.

The analysis of the trialkylamine concentration may be performed as follows. A Hewlett Packard Agilent 6890 gas chromatograph with a 30 m×0.32 mm×5 μm CP Volamine (Varian) column was set to provide a heating profile of 50° C. (5 min. hold) followed by ramping to 260° C. at 20° C./min. (2.5 min. hold) for a total run time of 18 minutes using constant pressure mode and an initial flow of 1.9 mL/min. Nominal initial pressure is 10 psi and the linear velocity is 33 cm/sec using helium as the carrier gas. The split inlet mode with a split ratio of 21.3:1 and a split flow of 40 mL/min. is used at an inlet temperature of 270° C. and a total inlet flow of 44.3 mL/min. A Tekmar headspace autosampler operating at a headspace pressure of 15 psi, a platen temperature of 75° C. is used to provide a 230 μL sample. Sample equilibration time is set to 5 min. The transfer line temperature, needle temperature, and injection valve/loop temperature are set at 200° C. A flame ionization detector operating at 250° C., a hydrogen flow of 40 mL/min., an air flow of 450 mL/min. and a make-up gas of nitrogen at a flow of 45 mL/min. is used for detection.

Samples are prepared by weighing approximately 1 gram of sample into a headspace vial and recording the weight. Each sample is prepared in duplicate, one for direct analysis and one for standard addition of a calibration standard mixture. Approximately 0.5 grams of trisodium phosphate is added to each sample to facilitate volatilization of the amine impurities. Five mL of water is added to each sample and the vial is capped with a crimp-top cap.

Analysis of the quaternary trialkylammonium compound may be performed by High Performance Liquid Chromatography (HPLC) according to the following procedure. An HPLC unit including an Agilent model G1310A pump, Agilent model G1322A degasser, and a VICI ACU1050 Manual Injector is used. The column is a Waters Nova-pak C-18, 8 mm×10 cm, Radial-PAC cartridge. Detection is accomplished by an Agilent model G1362A RID (refractive index). HP Chemstation is used for integration. Typical sample size is 75 μL. Flow is set at 0.8 mL/min. The mobile phase comprises ½ PIC (Paired Ion Chromatography), prepared as 71.50 g sodium perchlorate, anhydrous, 3.98 g octane sulfonic acid (sodium salt), 1800 g distilled water, and 200 g methanol. Samples were diluted to 1 weight percent in mobile phase prior to injection. Other concentration may be used provided the concentration is suitable for detection.

In other embodiments the invention provides a method of making a quaternary trialkylammonium halide composition. In particular embodiments, the method includes providing a primary-halo-dihydroxyalkane and a trialkylamine in a stoichiometric excess with respect to the primary-halo-dihydroxyalkane under reaction conditions to provide an intermediate reaction mixture; reducing the pH of the intermediate reaction mixture; and isolating the quaternary trialkylammonium halide composition by crystallization with a polar organic solvent.

In some embodiments, the primary-halo-dihydroxyalkane is selected from the group consisting of primary-halo-dihydroxyalkanes following the formula:

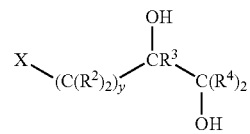

where the $R^2$, $R^3$, and $R^4$ groups are each individually selected from the group consisting of hydrogen, hydroxide, alkyl groups having from 1 to 12, particularly 1 to about 6, carbon atoms, and hydroxy alkyl groups having from 1 to 12, particularly 1 to about 6, carbon atoms; wherein y ranges from 0 to 12, preferably 0 to about 6, 0 to 3, or y is 1; wherein X is selected from the group consisting of fluoride, chloride, bromide, and iodide. In some embodiments, the primary-halo-dihydroxyalkane is 3-chloro-1,2 dihydroxypropane.

The trialkylamine may be selected from any desirable amine having alkyl groups individually selected from alkyl groups having from 1 to 12, particularly 1 to about 6 carbon atoms, particularly 1 to 3 carbon atoms, more particularly 1 carbon atom. Other suitable alkyl groups may be substituted or branched alkyl groups, or substituted or branched aryl groups, particularly groups having from 1 to 12 carbon atoms, particularly 1 to about 6 carbon atoms, more particularly 1 to 4 carbon atoms. Particularly suitable trialkylamines include trimethylamine, triethylamine, and tri-n-propylamine, dimethyl dodecylamine, tri-n-butylamine, tri-n-hexylamine, dimethylmonoethylamine, dimethylmono-n-butylamine, dimethylcyclohexylamine, dimethyl-monoisopropylamine, methylethyl-n-propylamine, methylethyl-n-butylamine, methyl dialkyl amines, and other tertiary amines having linear, branched, or cyclic hydrocarbon groups each independently containing from 1 to 12 carbon atoms.

In particular embodiments, the primary-halo-dihydroxyalkane is 3-chloro-1,2 dihydroxypropane and the trialkylamine is trimethylamine.

Whatever trialkylamine is selected, it is typically provided in a stoichiometric excess. In particular embodiments, the term "stoichiometric excess" means that a molar ratio of at least 1 to about 3 moles of the trialkylamine is provided for each mole of the primary-halo-dihydroxyalkane. In a particular embodiment, the molar ratio of the trialkylamine to the primary-halo-dihydroxyalkane ranges from about 1.0 to about 1.5, preferably 1.1 to 1.3 mole of the trialkylamine are provided for every mole of the primary-halo-dihydroxyalkane. While any excess amount of the trialkylamine may be used, large excesses of the amine may be difficult to remove. However, too little trialkylamine may result in incomplete reaction.

Any suitable reaction conditions may be used. Typically, the primary-halo-dihydroxyalkane is combined with an aqueous solution of the trialkylamine. However, any sources of the reactants may be used. The reaction temperature may range from about −20° C. to about 25° C. Excess heat should be avoided. Typical reaction times range from a few minutes to several days or more. The resulting mixture is treated to reducing its pH.

The pH of the reaction mixture may be reduced by any desirable means. In some embodiments, the pH may be reduced by adding one or more acids. The acid should be selected to reduce the pH without degrading the desired products. Any mineral or organic acid may be used. In other embodiments, the pH is reduced by physically removing at least some of the residual excess trialkylamine or other volatile components of the reaction mixture. In a particular embodiment, the alkylamine is removed by applying a reduced pressure to the reaction vessel or container. In other embodiments, the reaction mixture is sparged with an inert gas to remove the trialkylamine. Any gas that is inert to the desired product may be used. In some embodiments, the inert gas is air, oxygen, nitrogen, argon, or a gaseous alkane or alkene, and mixtures thereof may be used. Typically, however, nitrogen is used as the inert gas, particularly when the trialkylamine is trimethylamine. Whatever method is used, the pH is typically reduced to a value in the range of from about 3 to about 10, preferably about 4 to about 9, or about 5 to about 8. In some embodiments, the pH is reduced to a value in the range of about 6 to about 7.

In certain embodiments of the methods described herein, the method does not include heating the intermediate reaction mixture to remove one or more volatile components. In some embodiments, the method does not include heating the intermediate reaction mixture to remove volatile components when the reaction mixture has a pH of 8 or more. In other embodiments, the pH is less than 7.5, less than 7.0, less than 6.5, or less than 6.0 before a temperature greater than 25° C. is applied. Lower pH values such as 5.5, 5.0, 4.5 4.0, or 3.0 may also be achieved before a temperature greater than 25° C. is applied to the mixture.

In some embodiments, the method does not include heating the intermediate reaction mixture to remove volatile components when the reaction mixture has an undesirable level of trialkylamine, particularly where the amine is trimethylamine. Thus, in particular embodiments, the trialkylamine concentration is about 5000 ppm or less, about 4000 ppm or less, about 2000 ppm or less, or about 1000 ppm or less. In other embodiments, the trialkylamine concentration is about 500 ppm or less, about 250 ppm or less, about 100 ppm, about 50 ppm or less, about 25 ppm or less, or about 10 ppm or less before a temperature greater than 25° C. is applied to the mixture. In such embodiments, lower concentrations of trialkylamine are generally beneficial.

Isolating the quaternary trialkylammonium halide composition may be performed by treatment with any suitable solvent. In particular embodiments, the solvent is a polar organic solvent such as a halogenated hydrocaron solvent, such as methylene chloride, or tetrahydrofuran. In other embodiments, the solvent is selected from the group consisting of alcohols having from 3 to 20 carbon atoms. Particularly useful alcohols include propanol, isopropanol, butanols, and hexanols. Isopropanol is particularly useful. Once the solvent has been selected, precipitation of the quaternary trialkylammonium halide from the intermediate reaction mixture and the polar organic solvent may be induced by any suitable means. In some embodiments, the precipitation is induced upon the addition of the polar organic solvent. In other embodiments, the mixture may be cooled until precipitation occurs. In some embodiments, the polar organic solvent is recovered and reused to recover additional portions of the quaternary trialkylammonium halide composition in a subsequent isolation step of the method for making the compostions as described herein. In some embodiments, a seed crystal of previously isolated quaternary trialkylammonium halide composition is added to facilitate the crystallization.

In some embodiments, the isolation with the polar organic solvent is performed when the concentration of trialkylamine, such as trimethylamine, is present at an acceptable low level. Thus, in particular embodiments, the trialkylamine concentration is about 5000 ppm or less, about 4000 ppm or less, about 2000 ppm or less, or about 1000 ppm or less. In other embodiments, the trialkylamine concentration is reduced to about 500 ppm or less, about 250 ppm or less, about 100 ppm, about 50 ppm or less, about 25 ppm or less, about 10 ppm, or about 1 ppm or less before the isolation with the polar organic solvent. In such embodiments, lower concentrations of trialkylamine are generally beneficial.

In some embodiments, isolating the quaternary trialkylammonium halide further includes 1) separating the precipitated quaternary trialkylammonium halide from the remaining components of the reaction mixture and polar organic solvent and 2) drying the quaternary trialkylammonium halide. Any known method for separating may be used. Typically, the mixture is filtered to separate the precipitated quaternary trialkylammonium halide from the remaining components.

In particular embodiments, the invention provides a method of making a 2,3-dihydroxypropyltrimethylammonium chloride composition, wherein the method comprises providing 3-chloro-1,2-dihydroxypropane and trimethylamine in a molar ratio of 1 to about 3 moles with respect to the 3-chloro-1,2dihydroxypropane under reaction conditions to provide an intermediate reaction mixture; removing at least a portion of the remaining trimethylamine from the intermediate reaction mixture; and isolating the 2,3-dihydroxypropyltrimethylammonium chloride composition with a polar organic solvent, particularly an alcohol having 3 to about 20 carbon atoms, such as isopropyl alcohol.

The following example exemplifies an embodiment of the invention. It does not limit the invention as otherwise described and claimed herein. All numbers in the example are approximate values.

EXAMPLE 1

251 mL of 3-chloro-1,2-dihydroxypropane was added to a round bottom flask equipped with a stir bar, thermometer, and condenser. 837 mL of 25% aqueous trimethylamine was added to the reactor while stirring. The solution was allowed to stir for 16 hours at 15° C. The solution was sparged with nitrogen for six days during which time the pH decreases from about 11 to about 6. The solution was placed under reduced pressure of approximately 25 inches Hg for 24 hours at 65° C. The solution was then placed under reduced pressure of 30 inches of Hg for eight hours at 65° C. The solution was allowed to stand at ambient conditions for 48 hours. The solution was then placed under reduced pressure of 30 inches of Hg for four hours at 65° C. 200 mL of isopropanol was added to the solution and the product crystallizes. The product was filtered and placed in a nitrogen dry box for 24 hours and then in a vacuum oven at about 60° C. and at reduced pressure of 26 inches of Hg with a nitrogen sweep for 36 hours. The product was placed in a nitrogen dry box for 24 hours. The product was analyzed for trimethylamine via GC headspace analysis and had 3.2 ppm trimethylamine. Analysis by HPLC showed 100.0% purity of the 2,3-dihydroxypropyltrimethylammonium chloride.

EXAMPLE 2

110.5220 g of 3-chloro-1,2-dihydroxypropane was added to a 2 L beaker. 500 mL of 25% aqueous trimethylamine was added to the beaker while stirring. The solution was allowed to stir for 1.5 hours at room temperature. The solution was pH adjusted using concentrated hydrochloric acid to a pH of 6.5. The solution was placed under reduced pressure of 30 inches of Hg for thirty minutes at 65° C. The product was analyzed for trimethylamine via GC headspace analysis and had <1 ppm of trimethylamine.

EXAMPLE 3

251 mL of 3-chloro-1,2-dihydroxypropane was added to a round bottom flask equipped with a stir bar, thermometer, and condenser. 837 mL of 25% aqueous trimethylamine was added to the reactor while stirring. The solution was allowed to stir for 44 hours at 15° C. The solution was sparged with nitrogen for 13 days during time the pH decreased from about 11 to about 6. 200 mL of methanol was added to 400 mL of reaction solution and placed under reduced pressure of 30 inches Hg for four hours at 65° C. 200 mL of isopropanol was added to the solution and the solution was then placed under reduced pressure of 30 inches of Hg for two hours at 65° C. The solution was allowed to stand at ambient conditions for 16 hours. The solution was then placed under reduced pressure of 30 inches of Hg for five hours at 65° C. The solution was allowed to stand at ambient conditions for 16 hours. The solution was then placed under reduced pressure of 30 inches of Hg for two hours at 65° C. 200 mL of isopropanol was added to the solution and the product crystallized. The product was filtered and placed in a nitrogen dry box for 24 hours. There after the sample was placed in a vacuum oven at about 60° C. and reduced pressure of 26 inches of Hg with a nitrogen sweep for 36 hours. The product was placed in a nitrogen dry box for 24 hours. The product was analyzed for trimethylamine via GC headspace analysis and had 4.0 ppm of the trimethylamine. Analysis by HPLC shows 100.0% purity of the 2,3-dihydroxypropyltrimethylammonium chloride.

COMPARATIVE EXAMPLE 4

Example 8 of European Patent 0 257 619 was reproduced using the information disclosed therein. 40 mL of 30 w/v percent of an aqueous solution of trimethylamine is added to 10.40 g of 3-chloro-1,2-propanediol. After reacting for 2 hours at room temperature, the reaction mixture is evaporated to dryness to yield the product. Headspace analysis using the method described herein indicates that the composition has more than 4240 ppm trimethylamine.

While the invention has been described with respect to a limited number of embodiments, the specific features of one embodiment should not be attributed to other embodiments of the invention. No single embodiment is representative of all aspects of the inventions. Moreover, variations and modifications therefrom exist. For example, embodiments of the compositions described herein are substantially or essentially free of any component that has not been expressly recited as contained therein. Other components may be present so long as the recited features are met. In particular it is envisioned that the compositions may be used in formulations thereby reducing the absolute concentrations of the quaternary trialkylammonium compound and residual trialkylamine or protonated form thereof. Thus, the amounts or concentrations of the quaternary trialkylammonium compound and the trialkylamine compound or protonated form thereof in the composition may be determined relative to only the amounts of the quaternary trialkylammonium compound and the trialkylamine compound (and/or protonated form thereof) in such formulations. In some embodiments, the methods described herein provide compositions having improved color. In addition, some embodiments of the methods described herein consist of or consist essentially of the enumerated steps. In other embodiments, the steps are performed in a variety of chronological orders. The appended claims intend to cover all such variations and modifications as falling within the scope of the invention.

What is claimed is:

1. A composition comprising:
a quaternary trialkylammonium halide compound following the formula:

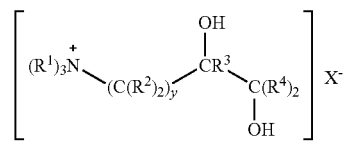

wherein the $R^1$ groups are each individually selected from the group consisting of alkyl groups having from 1 to 12 carbon atoms;
where the $R^2$, $R^3$, and $R^4$ groups are each individually selected from the group consisting of hydrogen, hydroxide, alkyl groups having from 1 to 12 carbon atoms, and hydroxy alkyl groups having from 1 to 12 carbon atoms;
wherein y ranges from 0 to 12;
wherein $X^-$ is selected from the group consisting of fluoride, chloride, bromide, and iodide;
wherein the quaternary trialkylammonium halide compound is present in an amount of at least 90 wt. percent; and
wherein the composition comprises not greater than 4000 ppm of a trialkylamine or protonated form thereof.

2. The composition of claim 1, wherein the quaternary trialkylammonium halide compound is a 2,3-dihydroxypropyltrialkylammonium chloride or a 3,4-dihydroxybutyltrialkylammonium chloride.

3. The composition of claim 1, wherein the quaternary trialkylammonium halide compound is 2,3-dihydroxypropyltrimethylammonium chloride.

4. The composition of claim 1, wherein the quaternary trialkylammonium halide compound is 2,3-dihydroxypropyltrimethylammonium chloride, and the trialkylamine is trimethylamine;
wherein the 2,3-dihydroxypropyltrimethylammonium chloride is present in an amount of at least 95 wt. percent; and
wherein the composition comprises not greater than 1000 ppm trimethylamine or protonated form thereof.

5. The composition of claim 4, wherein the 2,3-dihydroxypropyltrimethylammonium chloride is present in an amount of at least 99.5 wt. percent; and wherein the composition comprises not greater than 500 ppm trimethylamine or protonated form thereof.

6. The composition of claim 5, wherein the 2,3-dihydroxypropyltrimethylammonium chloride is present in an amount of at least 99.5 wt. percent; and wherein the composition comprises not greater than 25 ppm trimethylamine or protonated form thereof.

7. The composition of claim 6, wherein the 2,3-dihydroxypropyltrimethylammonium chloride is present in an amount of at least 99.5 wt. percent; and wherein the composition comprises not greater than 10 ppm trimethylamine or protonated form thereof.

8. The composition of claim 7, wherein the 2,3-dihydroxypropyltrimethylammonium chloride is present in an amount of at least 99.9 wt. percent; and wherein the composition comprises not greater than 1 ppm trimethylamine or protonated form thereof.

9. The composition of claim 1 wherein the concentrations are determined based on the amounts of the quaternary trialkylammonium halide and the trialkylamine or protonated form thereof in the composition.

10. A composition comprising at least 99.5 wt. percent 2,3-dihydroxypropyltrimethylammonium chloride and not greater than 25 ppm trimethylamine or protonated form thereof, wherein the concentrations are determined based on the amounts of 2,3-dihydroxypropyltrimethylammonium chloride and the trimethylamine in the composition.

11. A method of making a quaternary trialkylammonium halide composition, wherein the method comprises:
providing a primary-halo-dihydroxyalkane and a trialkylamine in a stoichiometric excess with respect to the primary-halo-dihydroxyalkane under reaction conditions to provide an intermediate reaction mixture; and
reducing the pH of the intermediate reaction mixture, wherein reducing the pH includes at least one of:
reducing the pH to a value in the range of from about 3 to about 10,
removing volatile impurities,
applying a reduced pressure, and
sparging the intermediate reaction mixture;
thereby affording the quaternary trialkylammonium halide composition.

12. The method of claim 11, wherein the primary-halo-dihydroxyalkane is selected from the group consisting of primary-halo-dihydroxyalkanes following the formula:

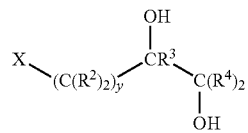

where the $R^2$, $R^3$, and $R^4$ groups are each individually selected from the group consisting of hydrogen, hydroxide, alkyl groups having from 1 to 12 carbon atoms, and hydroxy alkyl groups having from 1 to 12 carbon atoms;
wherein y ranges from 0 to 12;
wherein X is selected from the group consisting of fluoride, chloride, bromide, and iodide.

13. The method of claim 11, wherein the primary-halo-dihydroxyalkane is 3-chloro-1,2-dihydroxypropane and the trialkylamine is trimethylamine.

14. The method of claim 11, wherein the stoichiometric excess is a molar ratio of at least 1 to about 3 moles of the trialkylamine with respect to the primary-halo-dihydroxyalkane.

15. The method of claim 13, wherein the molar ratio of the trialkylamine to the primary-halodihydroxyalkane ranges from about 1.0 to about 1.5.

16. The method of claim 11, wherein the reducing the pH includes reducing the pH to a value in the range of from about 3 to about 10.

17. The method of claim 11, wherein the reducing the pH includes reducing the pH to a value in the range of from about 6 to about 7.

18. The method of claim 11, wherein reducing the pH includes removing volatile impurities.

19. The method of claim 11, wherein reducing the pH includes removing trimethylamine.

20. The method of claim 19, wherein further including an acid treatment.

21. The method of claim 11, wherein reducing the pH includes sparging the intermediate reaction mixture with an inert gas.

22. The method of claim 11, wherein the process does not include heating the intermediate reaction mixture to remove one or more volatile components.

* * * * *